(12) United States Patent  
Park et al.

(10) Patent No.: US 11,809,599 B2  
(45) Date of Patent: Nov. 7, 2023

(54) THREE-DIMENSIONAL MEDICAL IMAGE ANONYMIZATION METHOD AND APPARATUS

(71) Applicant: MEDICALIP CO., LTD., Gangwon-do (KR)

(72) Inventors: Sang Joon Park, Seoul (KR); Doo Hee Lee, Seoul (KR)

(73) Assignee: MEDICALIP CO., LTD.

( * ) Notice: Subject to any disclaimer, the term of this patent is extended or adjusted under 35 U.S.C. 154(b) by 0 days.

(21) Appl. No.: 17/840,953

(22) Filed: Jun. 15, 2022

(65) Prior Publication Data

US 2022/0405425 A1   Dec. 22, 2022

(30) Foreign Application Priority Data

Jun. 16, 2021   (KR) .................. 10-2021-0078058

(51) Int. Cl.
| | |
|---|---|
| *G06F 21/62* | (2013.01) |
| *G06T 7/187* | (2017.01) |
| *G06T 7/11* | (2017.01) |
| *G06T 7/13* | (2017.01) |
| *G16H 30/40* | (2018.01) |

(52) U.S. Cl.
CPC ............ *G06F 21/6254* (2013.01); *G06T 7/11* (2017.01); *G06T 7/13* (2017.01); *G06T 7/187* (2017.01); *G16H 30/40* (2018.01); *G06T 2200/04* (2013.01); *G06T 2207/10081* (2013.01); *G06T 2207/30196* (2013.01)

(58) Field of Classification Search
CPC ....... G06F 21/6254; G06T 7/187; G06T 7/11; G06T 7/13; G16H 30/40

USPC ......................................................... 726/27
See application file for complete search history.

(56) References Cited

U.S. PATENT DOCUMENTS

2016/0048944 A1* 2/2016 Ashmole ................ A61B 6/032  
                                                         382/131  
2019/0362536 A1* 11/2019 Kuhn .................... G06T 19/006  
(Continued)

FOREIGN PATENT DOCUMENTS

| EP | 3 188 058 A1 | 7/2017 |
| EP | 3188058 A1 * | 7/2017 |
| KR | 10-2020-0014396 | 2/2020 |

OTHER PUBLICATIONS

Tiancheng He; A Three-Dimensional Medical Image Segmentation App Using graphic Theory; IEEE:2017; pp. 268-271.*

(Continued)

*Primary Examiner* — Monjur Rahim  
(74) *Attorney, Agent, or Firm* — Klarquist Sparkman, LLP

(57) ABSTRACT

A method and apparatus for anonymizing a three-dimensional medical image are provided. The apparatus determines a skin region of a three-dimensional medical image, generates a human mask based on a human tissue region of the three-dimensional medical image, the human tissue region including various organs, generates a skin expansion region in which the skin region of the three-dimensional medical image is expanded, generates an anonymization region obtained by removing a region corresponding to the human mask from the skin expansion region, and changes brightness values of voxels corresponding to the anonymization region in the three-dimensional medical image to a predefined value or an arbitrary value.

7 Claims, 11 Drawing Sheets

(56) References Cited

U.S. PATENT DOCUMENTS

| | | | |
|---|---|---|---|
| 2019/0378607 A1* | 12/2019 | Chen | G16H 30/40 |
| 2020/0194117 A1* | 6/2020 | Krieger | G06N 3/0481 |
| 2021/0174477 A1* | 6/2021 | Shi | G06N 3/0454 |

OTHER PUBLICATIONS

Silva et al., "Face de-identification service for neuroimaging volumes," In *2018 IEEE 31st International Symposium on Computer-Based Medical Systems (CBMS)*, pp. 141-145, IEEE, 2018.

Milchenko et al., "Obscuring surface anatomy in volumetric imaging data," *Neuroinformatics* 11: 65-75, Jan. 2013.

* cited by examiner

THREE-DIMENSIONAL MEDICAL IMAGE ANONYMIZATION METHOD AND APPARATUS

CROSS REFERENCE TO RELATED APPLICATION

This application is based on and claims priority under 35 U.S.C. § 119 to Korean Patent Application No. 10-2021-0078058, filed on Jun. 16, 2021, in the Korean Intellectual Property Office, the disclosure of which is incorporated by reference herein in its entirety.

FIELD

One or more embodiments relate to a three-dimensional medical image anonymization method and apparatus, whereby a face or the shape of body parts on a three-dimensional medical image are de-identified.

The present invention is a research conducted with the support of the Ministry of Health and Welfare (task number: HI21C1074050021, task identification number: 202012E08, name of ministry: the Ministry of Health and Welfare, research management institution: the Korea Health Industry Development Institute, research project name: Establishment of Intensive Care-Centered Big Data and Development of AI-based CDSS, research task name: Establishment of Korean Intensive Care-Centered Big Data (K-MIMIC) and Development of AI-CDSS, managing institution: Seoul National University Hospital, research period: from Apr. 1, 2021 to Dec. 31, 2025).

DESCRIPTION OF THE RELATED ART

In a three-dimensional medical image captured using computed tomography (CT) or magnetic resonance imaging (MRI), a face or the shape of body parts of a photography subject are shown. When a three-dimensional medical image is to be used for big data, artificial intelligence, or other various purposes, it is necessary to protect personal information by de-identifying the face or the shape of body parts of the photography subject, in the three-dimensional medical image.

SUMMARY

One or more embodiments include a three-dimensional medical image anonymization method and apparatus, whereby personal information may be protected by de-identifying surface information, such as a face or the shape of body parts of a photography subject to be photographed, appearing in a three-dimensional medical image.

Additional aspects will be set forth in part in the description which follows and, in part, will be apparent from the description, or may be learned by practice of the presented embodiments of the disclosure.

According to one or more embodiments, a three-dimensional medical image anonymization method includes: determining a skin region of a three-dimensional medical image; generating a human mask based on a human tissue region of the three-dimensional medical image, the human tissue region including various organs; generating a skin expansion region in which the skin region of the three-dimensional medical image is expanded; generating an anonymization region obtained by removing a region corresponding to the human mask from the skin expansion region; and changing brightness values of voxels corresponding to the anonymization region in the three-dimensional medical image to a predefined value or an arbitrary value.

According to one or more embodiments, a three-dimensional medical image anonymization apparatus includes: a skin region extractor configured to determine a skin region of a three-dimensional medical image; a mask generator configured to generate a human mask based on a human tissue region of the three-dimensional medical image, the human tissue region including various organs; an expansion unit configured to generate a skin expansion region with respect to voxels constituting the skin region of the three-dimensional medical image; an anonymization region generator configured to generate an anonymization region obtained by removing a region corresponding to the human mask from the skin expansion region; and an information changing unit configured to change brightness values of voxels corresponding to the anonymization region in the three-dimensional medical image to a predefined value or an arbitrary value.

DETAILED DESCRIPTION

Figure 1:
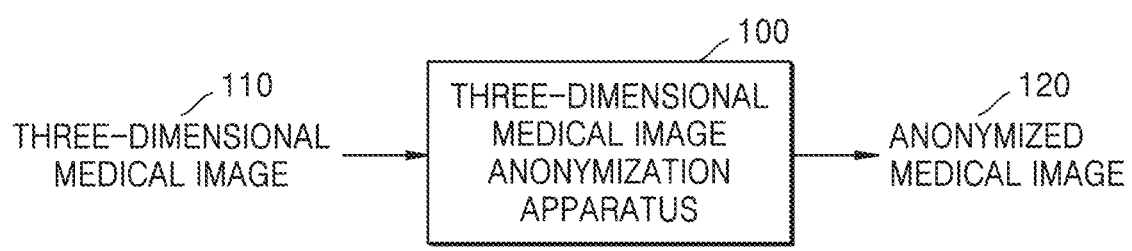
FIG. 1 illustrates an example of a three-dimensional medical image anonymization apparatus according to an embodiment of the present disclosure.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Hereinafter, a three-dimensional medical image anonymization method and apparatus are described with reference to the attached drawings.

FIG. 1 illustrates an example of a three-dimensional medical image anonymization apparatus according to an embodiment of the present disclosure.

Referring to FIG. 1, upon receiving a three-dimensional medical image 110 as an input, a three-dimensional medical image anonymization apparatus 100 (hereinafter, referred to as an 'anonymization apparatus') outputs an anonymized medical image 120 in which information regarding a surface boundary of the human body included in the three-dimensional medical image 110 is de-identified.

The three-dimensional medical image 110 may include a plurality of tomographic images obtained by tomography of all or a portion of the human body. For example, the three-dimensional medical image 110 may be a computed tomography (CT) image or a magnetic resonance imaging (MRI) image. The three-dimensional medical image 110 may be stored as a Digital Imaging and Communication in Medicine (DICOM) file. That is, the anonymization apparatus 100 may receive a DICOM file storing a three-dimensional medical image. In an embodiment, the anonymization apparatus 100 may receive the three-dimensional medical image 110 from a Picture Archiving and Communication System (PACS) system or the like, and anonymize the same, and store the three-dimensional medical image 120 that is anonymized, in the PACS system to replace the existing three-dimensional medical image, that is, the three-dimensional medical image 110.

When displaying the three-dimensional medical image 110, the anonymization apparatus 100 does not de-identify human body surface information, but removes the human body surface information from the three-dimensional medical image 110. Here, 'removal' refers to de-identification done by deleting human body surface information from the three-dimensional medical image 110 or de-identification done by changing the human body surface information included in the three-dimensional medical image 110. However, hereinafter, for convenience, description will focus on de-identification performed by changing human body surface information.

Figure 2:
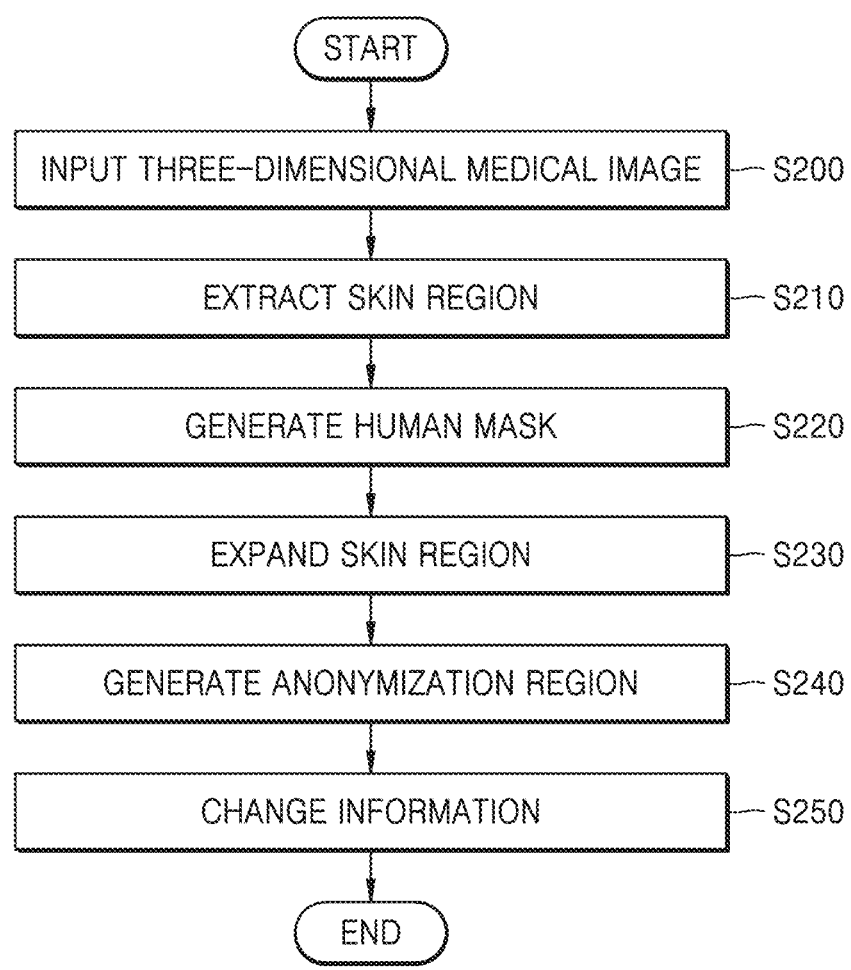
FIG. 2 is a flowchart of an example of a three-dimensional medical image anonymization method according to an embodiment of the present disclosure.

FIG. 2 is a flowchart of an example of a three-dimensional medical image anonymization method according to an embodiment of the present disclosure.

Referring to FIG. 2, the anonymization apparatus 100 receives a three-dimensional medical image in operation S200. Hereinafter, for convenience of description, it is assumed that the three-dimensional medical image is a CT image including a plurality of tomographic images.

The anonymization apparatus 100 extracts a skin region from a three-dimensional medical image in operation S210. In an embodiment, the anonymization apparatus 100 may extract a skin region by using brightness values of voxels constituting a three-dimensional medical image (e.g., a Hounsfield unit (HU) for a CT image). Because there is a certain difference in brightness values of voxels in a human body region and an air region in a three-dimensional medical image, the anonymization apparatus 100 may distinguish the human body region from the air region in each tomographic image of the three-dimensional medical image based on a predefined brightness value (for example, −1000 HU) for distinguishing the human body region from the air region.

Figure 3:
FIG. 3 illustrates an example of extraction of a skin region, according to an embodiment of the present disclosure.

The anonymization apparatus 100 may determine a skin region of a certain thickness, based on voxels of a human body region (i.e., voxels of a boundary of the human body region) that is in contact with an air region in each tomographic image. An example of distinguishing a skin region in a tomographic image constituting a three-dimensional medical image is shown in FIG. 3. For example, the anonymization apparatus 100 may extract a line-shaped skin region formed by connecting voxels on the boundary of a human body region that is in contact with an air region. As another example, the anonymization apparatus 100 may extract a skin region composed of a region of a certain thickness (e.g., several mm), which includes a certain number of voxels inwards from the voxels on the boundary of the human body region that is in contact with the air region.

In another embodiment, the anonymization apparatus 100 may use an artificial intelligence model to extract a skin region. An artificial intelligence model may be trained to predict a skin region by using learning data consisting of a three-dimensional medical image including segmentation information of the skin region. For example, a learning process of adjusting parameter values in an artificial intelligence model by comparing a skin region predicted by the artificial intelligence model with a skin region included in learning data (i.e., ground truth) may be performed. As examples of artificial intelligence models, various models according to the related art, such as a convolutional neural network (CNN) and a recurrent neural network (RNN), may be used. Also, other various algorithms for extracting a skin region, according to the related art, may be applied to the present embodiment.

The anonymization apparatus 100 generates a human mask including a human tissue region separately from the extraction of the skin region in operation S220. A human mask is used to prevent damage to image information of human tissue (e.g., bones, various organs, lesions, muscles, or fat, etc.) in a three-dimensional medical image in a process of de-identifying a surface of the three-dimensional medical image.

The anonymization apparatus 100 may generate a human mask by combining a plurality of human tissue regions obtained by segmenting various human tissues (e.g., various organs, such as a lung and the heart, bones, muscles, fat, etc.) based on a difference in brightness values of voxels of each human tissue. For example, as in the method disclosed in Korean Patent No. 10-1514003 "Lunglobe Extraction Method and Apparatus," human tissue may be segmented using different voxel brightness values (HU) for each tissue. As another example, the anonymization apparatus 100 may segment various human tissues of the human body by using an artificial intelligence model. Other various methods of segmenting bones or various organs from a three-dimensional medical image, according to the related art, may be applied to the present embodiment. In another embodiment, the anonymization apparatus 100 may generate a human mask by filling in empty regions between human tissue regions segmented using various methods according to the related art, such as morphological processing or 2D/3D hole filling.

The anonymization apparatus 100 generates a skin expansion region by expanding the skin region obtained from the three-dimensional medical image in operation S230. For example, the anonymization apparatus 100 may generate a skin expansion region by expanding a region in up, down, left, and right directions based on each voxel constituting the skin region in each tomographic image constituting the three-dimensional medical image. For example, the anonymization apparatus 100 may regard voxels that meet while proceeding in an arbitrary direction (up, down, left, and right) for a predefined number of times (or a predefined period of time) in each voxel, as voxels of the skin expansion region. As the anonymization apparatus 100 expands the skin region not only outwards from the human body region (that is, to the air region) but also inwards into the human body region, the anonymization apparatus 100 may completely de-identify surface boundary information of the three-dimensional medical image. For example, when the skin region is expanded only outwards from the skin, surface information of the human body may be obtained based on information about the inside of the skin, and when the skin region is expanded only inwards into the skin, on the contrary, surface information of the human body may be obtained based on information about the outside of the skin. Thus, in the present embodiment, the skin region is expanded in all directions, including an outward direction and an inward direction.

Figure 4:
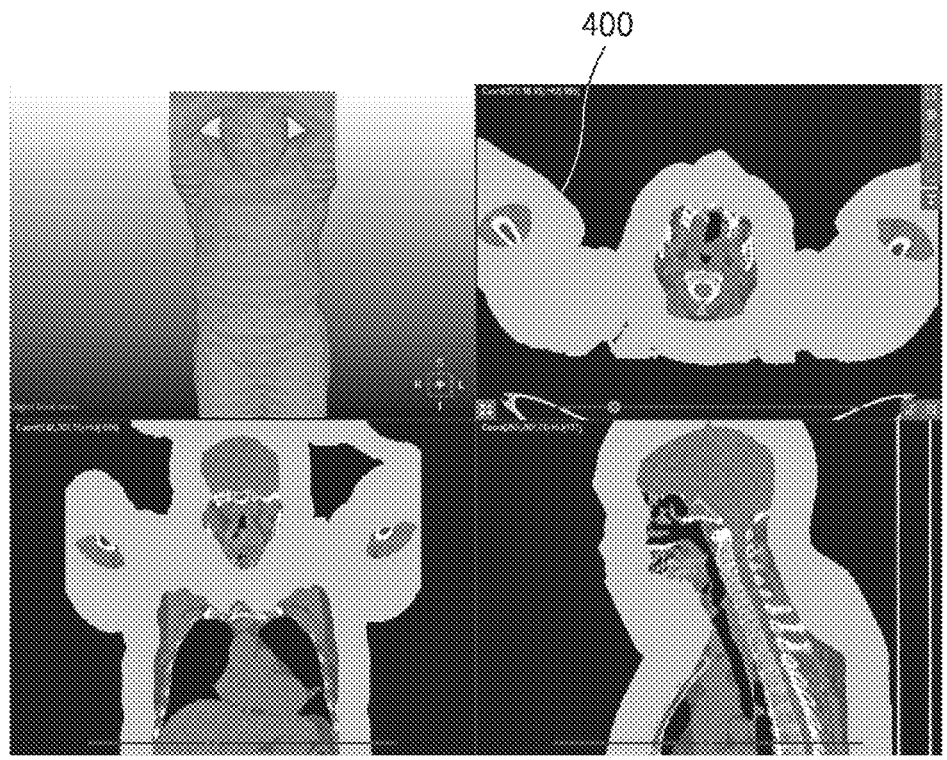
FIGS. 4 and 5 illustrate an example of expanding a skin region, according to an embodiment of the present disclosure.

However, when the skin region is expanded in both the outward and inward directions of the human body, information about an organ region, a bone region, and a lesion, or the like of a three-dimensional medical image may be invaded by the skin expansion region. For example, when a skin region located in the chest is expanded inwards, the skin expansion region may even invade the ribs or the lung region. Alternatively, in a three-dimensional medical image captured after raising the arms, as shown in FIG. 4, when expanding a skin region of the shoulder, a skin expansion region may invade the neck, the inside of the face, or even the brain region.

To address this, the anonymization apparatus 100 generates an anonymization region, which is a region obtained by subtracting a human mask from a skin expansion region in operation S240. The anonymization region is a region that de-identifies a surface of a three-dimensional medical image, but information about the skin surface still is left in the three-dimensional medical image without change. Therefore, the anonymization apparatus 100 changes and stores brightness values of voxels corresponding to the anonymization region in the three-dimensional medical image to a predefined brightness value or an arbitrary brightness value in operation S250. For example, the anonymization apparatus 100 may de-identify surface information by assigning an arbitrary brightness value to each voxel, for example, by assigning a first brightness value to a first voxel and a second brightness value to a second voxel among voxels of a three-dimensional medical image corresponding to an anonymization region. That is, all or some of the voxels corresponding to the anonymization region in the three-dimensional medical image may be changed to different brightness values.

FIG. 3 illustrates an example of extraction of a skin region, according to an embodiment of the present disclosure.

Referring to FIG. 3, a three-dimensional medical image may be displayed as a three-dimensional modeling image together with a sagittal plane image, a coronal plane image, and a cross-sectional image. The three-dimensional medical image is composed of a plurality of tomographic images, and each tomographic image is composed of voxels having a brightness value (e.g., HU).

Referring to the three-dimensional medical image, because brightness values of voxels constituting an air region 300 and a human body region 310 have contrast of a certain level or higher, the anonymization apparatus 100 may distinguish the human body region 310 from the air region 300 outside the human body region 310, based on a predefined brightness value, and extract a surface of the human body region 310 that is in contact with the air region 300 (that is, a skin region 320). As there may be also an air region inside the human body, such as a lung region, in a three-dimensional medical image, to easily detect only a skin region on the surface of the human body, the anonymization apparatus 100 may determine, from each tomographic image of the three-dimensional medical image, the air region 300 located outside (that is, a region having a brightness value less than a predefined brightness value), determine voxels of the human body region that is in contact with the air region 300, and obtain a skin region consisting of a line obtained by connecting the voxels or of a portion of a certain thickness inwards from the line into the skin. Moreover, other various methods of extracting a skin region, according to the related art, may be applied to the present embodiment, and the present disclosure is not limited to the method described with reference to FIG. 3.

Figure 5:
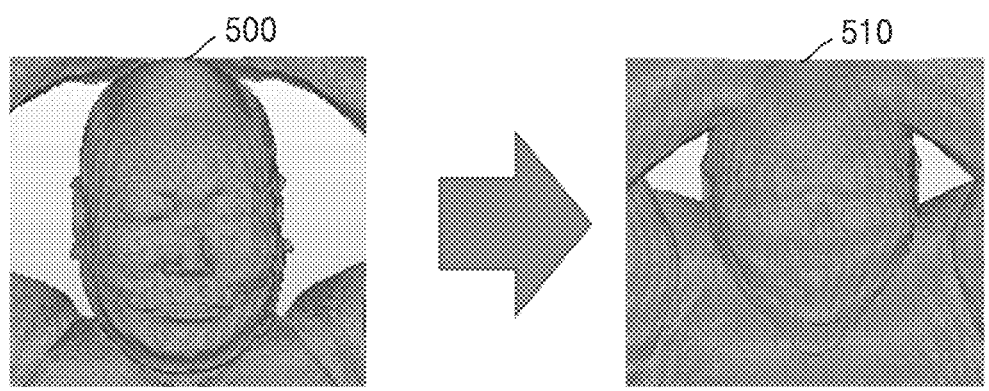

FIGS. 4 and 5 illustrate an example of expanding a skin region, according to an embodiment of the present disclosure.

Referring to FIGS. 4 and 5, the anonymization apparatus 100 may generate a skin expansion region 400 by expanding the skin region 320 obtained in the embodiment of FIG. 3 in an arbitrary direction. For example, the anonymization apparatus 100 may expand a skin region in an arbitrary direction by using, as a start point, each voxel corresponding to the skin region in each tomographic image of a three-dimensional medical image. Various methods for dilation of a certain region in an image, according to the related art, may be applied to the present embodiment. When the skin region is expanded, surface information of the three-dimensional medical image is de-identified (500->510), as shown in FIG. 5.

However, skin expansion is conducted in both outward and inward directions of a human body region, and thus, information about various human tissues inside the human body may be damaged. In order to prevent damage to the image information about the human tissue inside the human body, a human mask may be used, and an example thereof is shown in FIG. 6.

Figure 6:
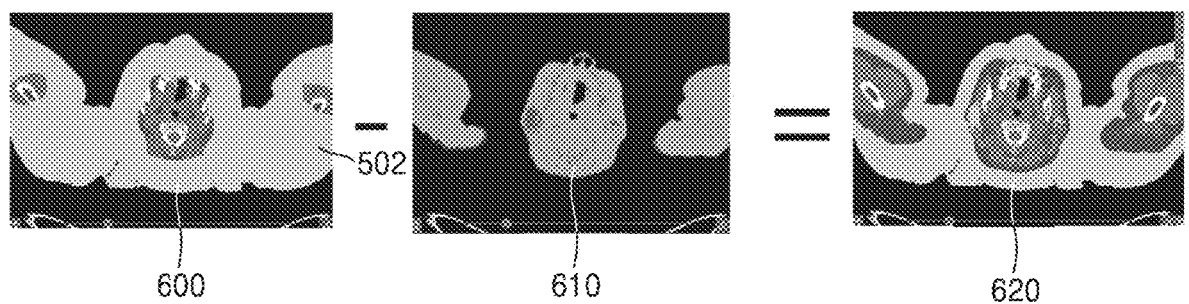
FIG. 6 illustrates an example of a method of generating an anonymization region, according to an embodiment of the present disclosure.

FIG. 6 illustrates an example of a method of generating an anonymization region, according to an embodiment of the present disclosure.

Referring to FIG. 6, the anonymization apparatus 100 generates an anonymization region 620, which is obtained by removing a region corresponding to a human mask 610, from a skin expansion region 600. For example, the anonymization apparatus 100 may generate the anonymization region 620, which is composed of voxels remaining after removing voxels belonging to the human mask 610 among voxels belonging to the skin expansion region 600 of each tomographic image constituting a three-dimensional medical image.

Figure 7:
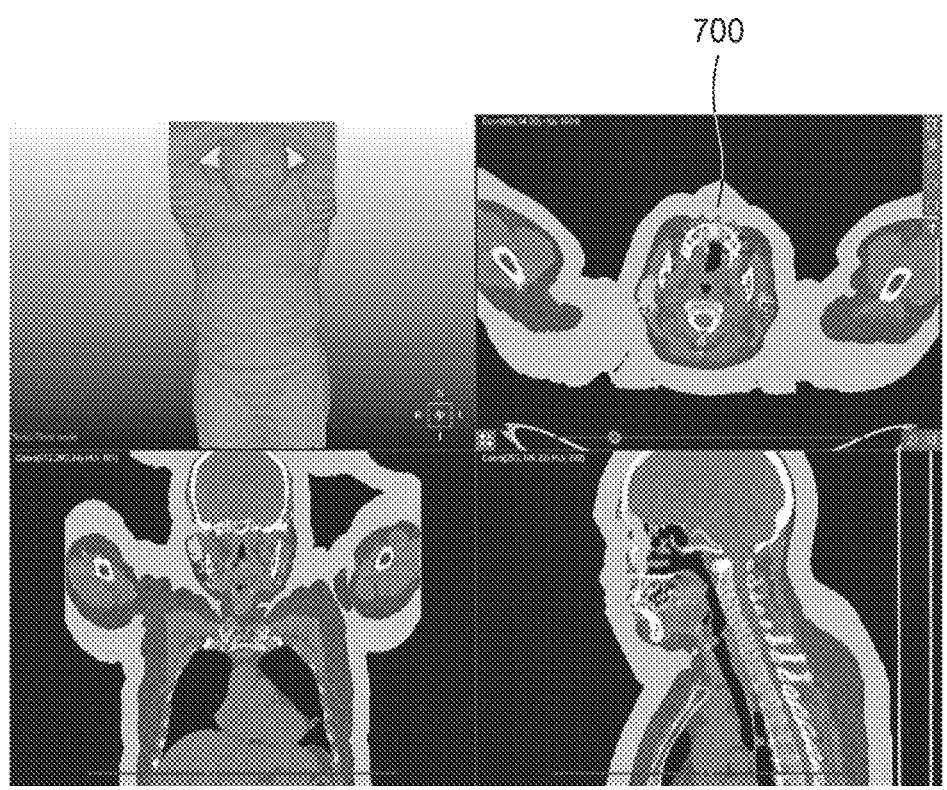
FIG. 7 illustrates an example of an anonymization region according to an embodiment of the present disclosure.

FIG. 7 illustrates an example of an anonymization region according to an embodiment of the present disclosure.

Referring to FIG. 7, an anonymization region 700 is a region generated through skin expansion, and thus, a skin surface of a three-dimensional medical image may be de-identified. Also, as the anonymization region is a region obtained by removing a region corresponding to a human mask from a skin expansion region, damage to image information of human tissue may be prevented.

Figure 8:
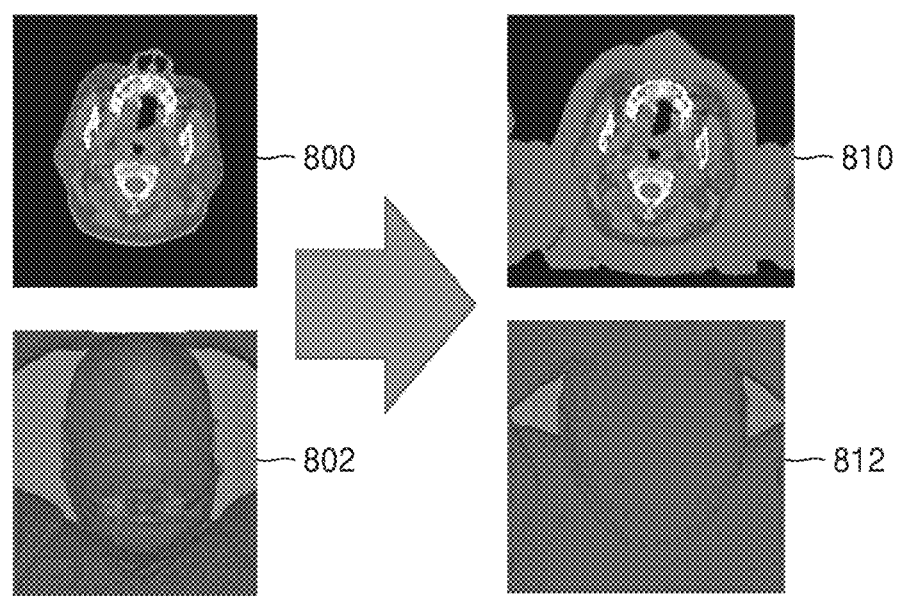
FIG. 8 illustrates an example of a three-dimensional medical image anonymized according to an embodiment of the present disclosure.

FIG. 8 illustrates an example of a three-dimensional medical image anonymized according to an embodiment of the present disclosure.

Figure 9:
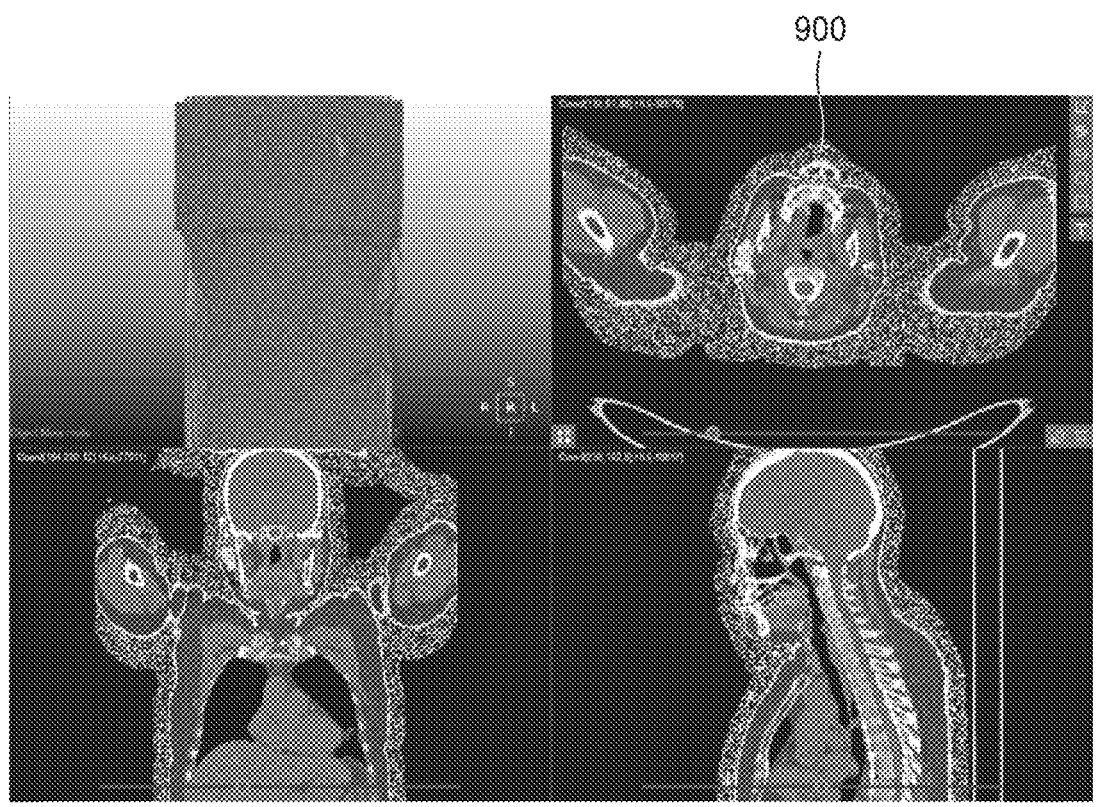
FIGS. 9 and 10 illustrate an example of changing an anonymization region to an arbitrary brightness value, according to an embodiment of the present disclosure.
Figure 10:
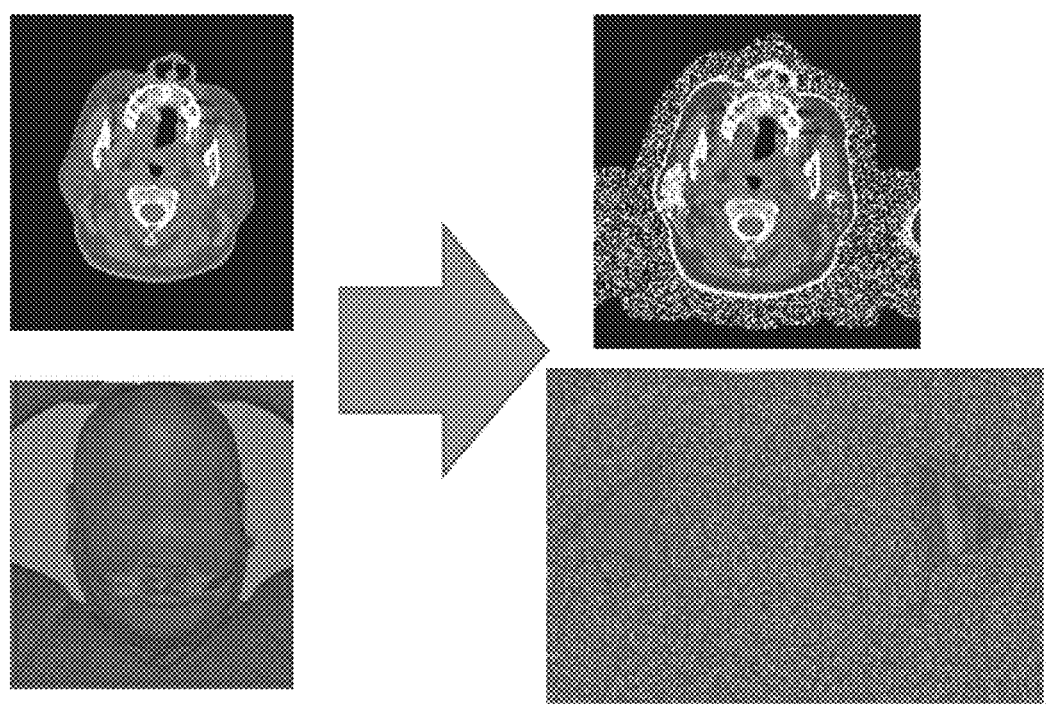

Referring to FIG. 8, when an anonymized region is stored and managed separately from a three-dimensional medical image, surface information, such as a face, remains in the three-dimensional medical image as it is, and thus, the face, etc. is identifiable (802). Accordingly, the anonymization apparatus 100 does not separately store and manage information about an anonymization region (700 in FIG. 7), but may change a brightness value of each voxel corresponding to the anonymization region in the three-dimensional medical image to a predefined brightness value or any arbitrary brightness value. According to the present embodiment, an example of changing brightness values of respective voxels corresponding to an anonymization region, to a uniform value, is shown, and an example in which the brightness values of the voxels corresponding to the anonymization region is changed to an arbitrary value is shown in FIGS. 9 and 10. In each tomography image 810 of the anonymized three-dimensional medical image, surface information is in a de-identified state, and thus, when a face region is modeled using the anonymized three-dimensional medical image (812), surface information about the face that is de-identified is displayed.

FIGS. 9 and 10 illustrate an example of changing an anonymization region to an arbitrary brightness value, according to an embodiment of the present disclosure.

Referring to FIGS. 9 and 10, the anonymization apparatus 100 may transform brightness values of voxels corresponding to an anonymization region 900 in a three-dimensional medical image to an arbitrary brightness value. In other words, extraction of surface information from the anonymized three-dimensional medical image through backtracking by generating random noise in the anonymization region 900 may be blocked fundamentally.

Figure 11:
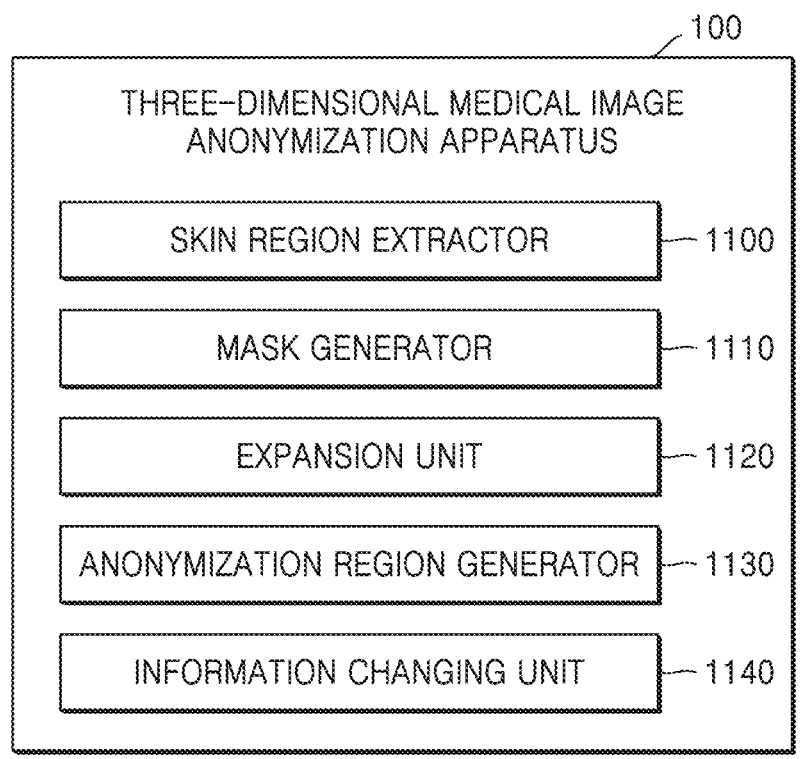
FIG. 11 illustrates an example of a configuration of a three-dimensional medical image anonymization apparatus according to an embodiment of the present disclosure.

FIG. 11 illustrates an example of a configuration of a three-dimensional medical image anonymization apparatus according to an embodiment of the present disclosure.

Referring to FIG. 11, a three-dimensional medical image anonymization apparatus 100 includes a skin region extractor 1100, a mask generator 1110, an expansion unit 1120, an anonymization region generator 1130, and an information changing unit 1140. The three-dimensional medical image anonymization apparatus 100 is implemented by a computer or server including a memory and a processor, and each component may be implemented by software, loaded in the memory, and then executed by the processor.

The skin region extractor 1100 extracts a skin region from a three-dimensional medical image. The skin region extractor 1100 may extract a skin region from a three-dimensional medical image by using contrast in brightness values between an air region and a human body region. Other various methods for segmenting a skin region from a three-dimensional medical image, according to the related art, may be applied to the present embodiment.

The mask generator 1110 generates a human mask by combining various human tissue regions (e.g., bones, organs, muscles, fat, blood vessels, etc.) segmented from the three-dimensional medical image. The mask generator 1110 may segment each human tissue region by using a difference in brightness values of human tissue, or segment each human tissue region by using an artificial intelligence model. In another embodiment, the mask generator 1110 may segment various human tissue regions through various existing human tissue segmentation algorithms. The mask generator 1110 may generate a human mask by combining human tissue regions, which are obtained by segmenting all of bones, various organs, muscles and, or segment only a few human tissue regions among human tissue regions according to an embodiment and then generate a human mask by combining the segmented human tissue regions. In other words, in a process of de-identification of human body surface information, a human body mask may be generated with respect to a human tissue region to be protected.

The expansion unit 1120 expands the skin region for de-identification of human body surface information. For example, the expansion unit 1120 may generate a skin expansion region formed by expanding a region in an arbitrary direction based on each voxel of the skin region.

The anonymization region generator 1130 generates an anonymization region obtained by removing a region corresponding to the human mask from the skin expansion region. By excluding the region of the human mask from the skin expansion region, damage to information of major organs in a three-dimensional medical image due to the skin expansion region may be prevented.

The information changing unit 1140 changes brightness values of voxels corresponding to the anonymization region in the three-dimensional medical image to a predefined brightness value or an arbitrary brightness value. For example, the information changing unit 1140 may assign an arbitrary brightness value to each voxel corresponding to the anonymization region. The information changing unit 1140 may change brightness values of the voxels of the anonymization region to various values according to an embodiment.

The present disclosure may also be implemented as computer-readable code on a computer-readable recording medium. The computer-readable recording medium includes all types of recording devices in which data readable by a computer system is stored. Examples of computer-readable recording media include read only memory (ROM), random access memory (RAM), a compact disk ROM (CD-ROM), a solid state disk (SSD), and optical data storage devices. In addition, the computer-readable recording medium is distributed in a network-connected computer system so that the computer-readable code can be stored and executed in a distributed manner.

According to an embodiment of the present disclosure, all of a face or the shape of body parts or the like of a subject to be photographed, in a three-dimensional medical image may be de-identified. Instead of just deforming or covering a face or the shape of body parts of a subject when displaying a three-dimensional medical image, surface information of the body stored in the three-dimensional medical image itself may be transformed to fundamentally prevent the possibility of exposure of personal information.

While the present disclosure has been particularly shown and described with reference to embodiments thereof, it will be understood by those of ordinary skill in the art that various changes in form and details may be made therein without departing from the spirit and scope of the present disclosure as defined by the appended claims. Thus, the disclosed embodiments should be considered in a descriptive sense only and not for purposes of limitation. Therefore, the scope of the present disclosure is defined not by the detailed description of the present disclosure but by the appended claims, and all differences within the scope will be construed as being included in the present disclosure.

We claim:

1. A three-dimensional medical image anonymization method comprising:
   determining a skin region of a three-dimensional medical image;
   generating a human mask based on a human tissue region segmented from the three-dimensional medical image through segmentation algorithm, the human tissue region including bones and organs inside a human body, excluding the skin region, wherein the human mask represents a human tissue region to be protected from anonymization;

generating a skin expansion region in which the skin region of the three-dimensional medical image is expanded;

generating an anonymization region obtained by removing a region corresponding to the human mask from the skin expansion region; and changing brightness values of voxels corresponding to the anonymization region in the three-dimensional medical image to a predefined value or an arbitrary value, wherein the determining of the skin region comprises determining, as the skin region, a region of a predefined thickness inwards into the human body with respect to a boundary portion of the human body in the three-dimensional medical image, wherein the generating of the skin expansion region comprises expanding the skin region in both an outward direction and an inward direction of the human body with respect to voxels of the skin region, and the skin expansion region comprises all of the skin region, a region expanded outwards from the human body, and a region expanded inwards into the human body.

2. The three-dimensional medical image anonymization method of claim 1, wherein the three-dimensional medical image comprises a computed tomography (CT) image.

3. The three-dimensional medical image anonymization method of claim 1, wherein the determining of the skin region comprises determining, as the skin region, a region of a predefined thickness inwards into the human body with respect to a boundary portion of the human body in the three-dimensional medical image or determining the skin region by using an artificial intelligence model for segmenting the skin region from the three-dimensional medical image.

4. The three-dimensional medical image anonymization method of claim 1, wherein the generating of the human mask comprises:

segmenting human tissue regions including bones and organs from the three-dimensional medical image by using a human tissue segmentation algorithm; and generating the human mask by filling empty regions between the segmented human tissue regions.

5. The three-dimensional medical image anonymization method of claim 1, wherein the generating of the skin expansion region comprises expanding a region in up, down, left, and right directions with respect to each voxel of the skin region.

6. A three-dimensional medical image anonymization apparatus comprising:

a skin region extractor configured to determine a skin region segmented from a three-dimensional medical image through segmentation algorithm;

a mask generator configured to generate a human mask based on a human tissue region of the three-dimensional medical image, the human tissue region including bones and organs inside a human body, excluding the skin region, wherein the human mask represents a human tissue region to be protected from anonymization;

an expansion unit configured to generate a skin expansion region with respect to voxels constituting the skin region of the three-dimensional medical image;

an anonymization region generator configured to generate an anonymization region obtained by removing a region corresponding to the human mask from the skin expansion region; and an information changing unit configured to change brightness values of voxels corresponding to the anonymization region in the three-dimensional medical image to a predefined value or an arbitrary value, wherein the determining of the skin region comprises determining, as the skin region, a region of a predefined thickness inwards into the human body with respect to a boundary portion of the human body in the three-dimensional medical image, wherein the expansion unit is configured to expand the skin region in both an outward direction and an inward direction of the human body with respect to voxels of the skin region, and the skin expansion region comprises all of the skin region, a region expanded outwards from the human body, and a region expanded inwards into the human body.

7. A non-transitory computer-readable recording medium having recorded thereon a computer program for executing the method of claim 1.

* * * * *